（12）United States Patent
Okazaki et al.

(10) Patent No.: US 8,915,836 B2
(45) Date of Patent: Dec. 23, 2014

(54) ENDOSCOPE, GUIDE UNIT, GUIDE WIRE, MEDICAL-DEVICE GUIDING SYSTEM, AND MEDICAL-DEVICE GUIDING METHOD

(75) Inventors: Yoshiro Okazaki, Tokyo (JP); Hiromu Ikeda, Tokyo (JP)

(73) Assignee: Olympus Corporation, Tokyo (JP)

( * ) Notice: Subject to any disclaimer, the term of this patent is extended or adjusted under 35 U.S.C. 154(b) by 452 days.

(21) Appl. No.: 13/022,930

(22) Filed: Feb. 8, 2011

(65) Prior Publication Data

US 2012/0203066 A1   Aug. 9, 2012

(30) Foreign Application Priority Data

Feb. 3, 2011   (JP) ................. 2011-021820

(51) Int. Cl.
    *A61B 1/00*    (2006.01)
    *A61M 25/09*   (2006.01)
    *A61B 1/01*    (2006.01)
    *A61B 1/04*    (2006.01)

(52) U.S. Cl.
    CPC .............. *A61B 1/01* (2013.01); *A61M 25/09* (2013.01); *A61B 1/00154* (2013.01); *A61B 1/00087* (2013.01); *A61M 2025/09116* (2013.01)
    USPC ........................... 600/104; 600/114; 600/153

(58) Field of Classification Search
    USPC ..................................... 600/104, 106, 117
    See application file for complete search history.

(56) References Cited

U.S. PATENT DOCUMENTS

| 5,882,293 | A  | * | 3/1999 | Ouchi | 600/104 |
| 6,991,602 | B2 | * | 1/2006 | Nakazawa et al. | 600/101 |
| 7,670,282 | B2 | * | 3/2010 | Mathis | 600/104 |
| 7,691,050 | B2 | * | 4/2010 | Gellman et al. | 600/29 |
| 7,775,968 | B2 | * | 8/2010 | Mathis | 600/104 |
| 8,747,297 | B2 | * | 6/2014 | Miyoshi et al. | 600/101 |
| 2003/0088153 | A1 | * | 5/2003 | Carrillo et al. | 600/114 |
| 2006/0224175 | A1 | * | 10/2006 | Vrba | 606/200 |
| 2006/0270900 | A1 | * | 11/2006 | Chin et al. | 600/104 |

FOREIGN PATENT DOCUMENTS

| JP | 2003-116777 A | 4/2003 |
| JP | 3432893       | 5/2003 |

OTHER PUBLICATIONS

English language abstract only of Japanese Publication No. JP 08-000546 published Jan. 9, 1996.

* cited by examiner

*Primary Examiner* — Alireza Nia
(74) *Attorney, Agent, or Firm* — Scully, Scott, Murphy & Presser, P.C.

(57) ABSTRACT

An endoscope and a surgical instrument are easily manipulated to desired positions and orientations independently while the state of treatment with the surgical instrument can be easily observed using an endoscopic image. Provided is a medical-device guiding method comprising a U-shape forming step of placing both ends of a guide wire outside the pericardium and placing the guide wire, with an intermediate portion curved in a substantially U-shape in the pericardial cavity; an endoscope inserting step of inserting an endoscope into the pericardial cavity along the guide wire from one end of the ends placed outside the pericardium in the U-shape forming step; a guide-unit inserting step of inserting the guide unit into the pericardial cavity along the guide wire from the other of the ends placed outside the pericardium in the U-shape forming step; and an opposing step of opposing the distal end portions of the endoscope and the guide unit, which are inserted into the pericardial cavity in the endoscope inserting step and the guide-unit inserting step, respectively, at intermediate positions of the guide wire.

3 Claims, 18 Drawing Sheets

ENDOSCOPE, GUIDE UNIT, GUIDE WIRE, MEDICAL-DEVICE GUIDING SYSTEM, AND MEDICAL-DEVICE GUIDING METHOD

CROSS REFERENCE TO RELATED APPLICATIONS

This application is based on Japanese Patent Application No. 2011-21820, the content of which is incorporated herein by reference.

BACKGROUND OF THE INVENTION

1. Field of the Invention

The present invention relates to an endoscope, a guide unit, a guide wire, a medical-device guiding system, and a medical-device guiding method.

2. Description of Related Art

An endoscope in which an observation window and an opening of a channel can be made to face each other is known (for example, see the Publication of Japanese Patent No. 3432893). With such an endoscope, an image of a surgical instrument taken in and out of the channel is acquired from the front. That is, an operative site can be treated easily and accurately with the surgical instrument without the operative site and the distal end of the surgical instrument being hidden behind the shadow of the mantle of the surgical instrument and being lost to sight in an endoscopic image.

The interior of the pericardial cavity between the heart and the pericardium that surrounds the heart requires complicated manipulation of the endoscope as compared with the case of the interior of a lumen, for which manipulation in the front-to-back direction is sufficient.

BRIEF SUMMARY OF THE INVENTION

An object of the present invention is to provide an endoscope, a guide unit, a guide wire, a medical-device guiding system, and a medical-device guiding method in which the endoscope and a surgical instrument can be easily manipulated to desired positions and orientations independently while the state of treatment with the surgical instrument can be easily observed using an endoscopic image.

To achieve the above object, the present invention provides the following solutions.

A first aspect of the present invention is an endoscope comprising a long narrow inserted portion that can be inserted into the pericardial cavity; and a guide wire fixed to the inserted portion and extending forward from the distal end of the inserted portion.

A second aspect of the present invention is a guide unit comprising a long narrow tube member that can be inserted into the pericardial cavity and having a lumen in which a surgical instrument is to be inserted formed in the longitudinal direction; and a guide wire fixed to the tube member and extending forward from the distal end of the tube member.

A third aspect of the present invention is a guide wire having a branch wire branching in an intermediate position in the longitudinal direction.

A fourth aspect of the present invention is a guide wire that guides, in the pericardial cavity, an inserted portion provided at an endoscope and a tube member provided at a guide unit, wherein the guide wire is shaped in a convex form curved at a predetermined curvature in an intermediate position in the longitudinal direction and has a flexibility lower than that of the inserted portion or the tube member.

A fifth aspect of the present invention is a guide wire that guides an inserted portion provided at an endoscope and a tube member provided at the guide unit in the pericardial cavity, wherein the guide wire has a first curved portion that is curved in a substantially U-shape in an intermediate position in the longitudinal direction and a second curved portion at which one end of the first curved portion is curved in a curved shape at a predetermined angle with respect to the other end, wherein the first curved portion and the second curved portion have a flexibility lower than that of the inserted portion and the tube member.

A sixth aspect of the present invention is a medical-device guiding system comprising a guide wire having the flexibility to be able to curve in a substantially U-shape in the pericardial cavity; and a guide unit including a long narrow flexible tube member in which a first lumen in which the guide wire is inserted and a second lumen in which a surgical instrument is inserted are formed in the longitudinal direction, wherein the first lumen has a through-hole which is disposed at a certain distance therefrom in the longitudinal direction and into which the guide wire is inserted; and the guide wire has a stopper, in an intermediate position in the longitudinal direction, having an outside diameter larger than the hole diameter of the through-hole.

A seventh aspect of the present invention is a medical-device guiding system comprising a guide wire having the flexibility to be able to curve in a substantially U-shape in the pericardial cavity; an endoscope having a long narrow inserted portion which can be inserted into the pericardial cavity and in which a channel in which the guide wire is inserted is formed in the longitudinal direction; and a guide unit including a long narrow tube member which can be inserted into the pericardial cavity and in which a first lumen in which the guide wire is inserted and a second lumen in which a surgical instrument is inserted are formed in the longitudinal direction, wherein the guide wire has two stoppers provided at intermediate positions in the longitudinal direction, with a distance corresponding to the depth of field of the endoscope therebetween, and having outside diameters larger than the diameters of openings at the distal ends of the channel and the first lumen.

An eighth aspect of the present invention is a medical-device guiding method comprising a U-shape forming step of placing both ends of a guide wire outside the pericardium and placing the guide wire, with an intermediate portion curved in a substantially U-shape in the pericardial cavity; an endoscope inserting step of inserting an endoscope into the pericardial cavity along the guide wire from one of the ends placed outside the pericardium in the U-shape forming step; a guide-unit inserting step of inserting the guide unit into the pericardial cavity along the guide wire from the other of the ends placed outside the pericardium in the U-shape forming step; and an opposing step of opposing the distal end portions of the endoscope and the guide unit, which are inserted into the pericardial cavity in the endoscope inserting step and the guide-unit inserting step, respectively, at intermediate positions of the guide wire.

BRIEF DESCRIPTION OF THE SEVERAL VIEWS OF THE DRAWINGS

FIG. 22A and FIG. 22B are diagrams illustrating the operation of the release mechanism in FIG. 21, in which FIG. 22A shows a state in which the protruding portion engages with a row of teeth, and FIG. 22B shows a state in which the engagement of the protruding portion and the row of teeth is released;

DETAILED DESCRIPTION OF THE INVENTION

An endoscope 1, a guide unit 10, a guide wire 20, and a medical-device guiding system 100 equipped with the same according to an embodiment of the present invention, as well as a medical-device guiding method using the medical-device guiding system 100, will be described hereinbelow with reference to the drawings.

Figure 1:
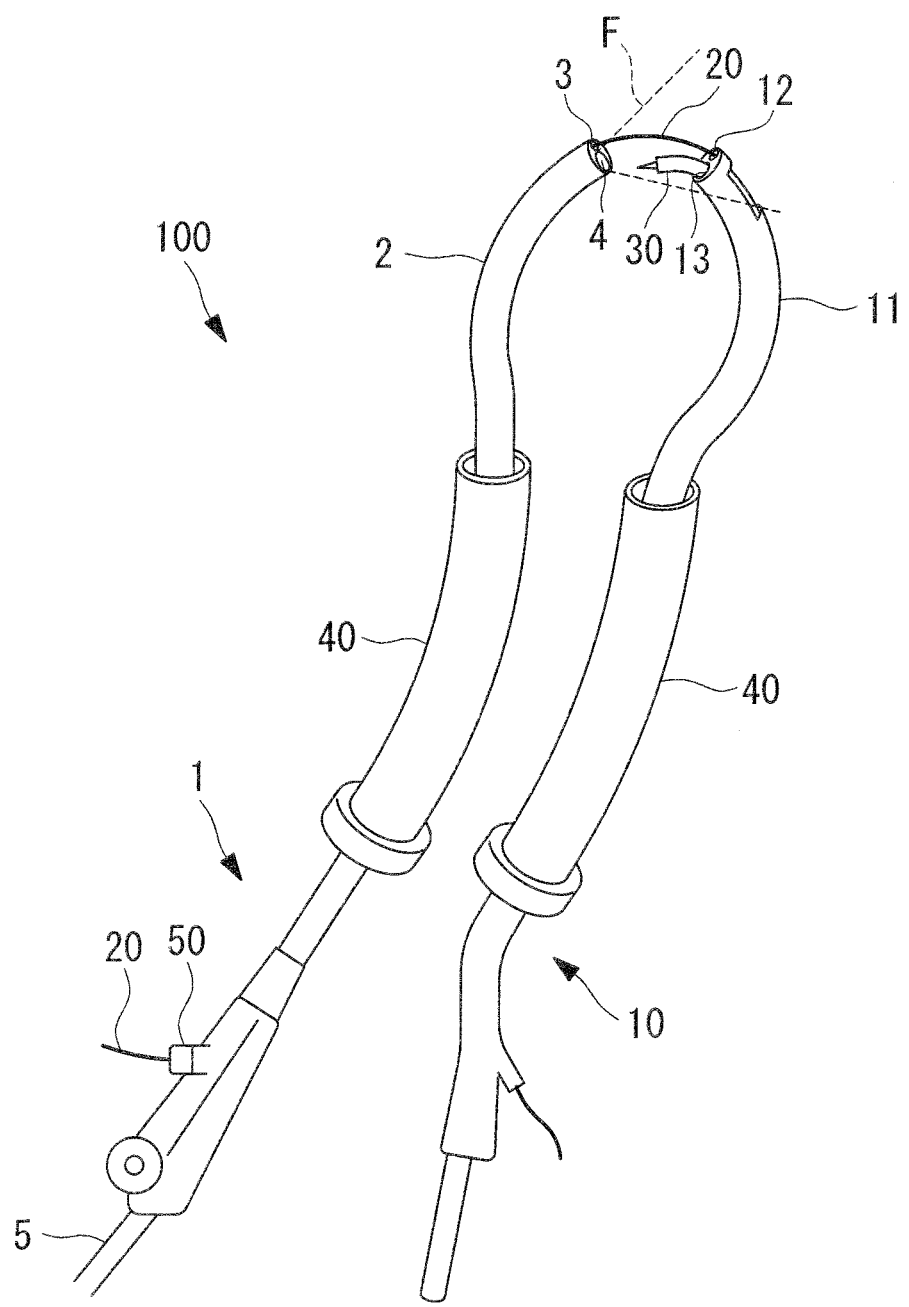
FIG. 1 is a diagram showing the overall configuration of a medical-device guiding system according to an embodiment of the present invention.

As shown in FIG. 1, the medical-device guiding system 100 according to this embodiment is equipped with the endoscope 1, the guide unit 10 that guides a surgical instrument 30, the guide wire 20 that guides the endoscope 1 and the guide unit 10, and two tubular sheaths 40 into which the endoscope 1 and the guide unit 10 are individually inserted.

The endoscope 1 is of a direct view type for observing a front field of view F and is equipped with a long narrow inserted portion 2 that can be inserted into the pericardial cavity A, a channel 3 formed through the inserted portion 2 in the longitudinal direction, in which the guide wire 20 is inserted, and an observation window 4 provided at the distal end face of the inserted portion 2. The endoscope 1 acquires an image of external light collected through the observation window 4 with an optical system (not shown). Acquired image data is displayed on a monitor (not shown) via a cable 5.

Figure 2A:
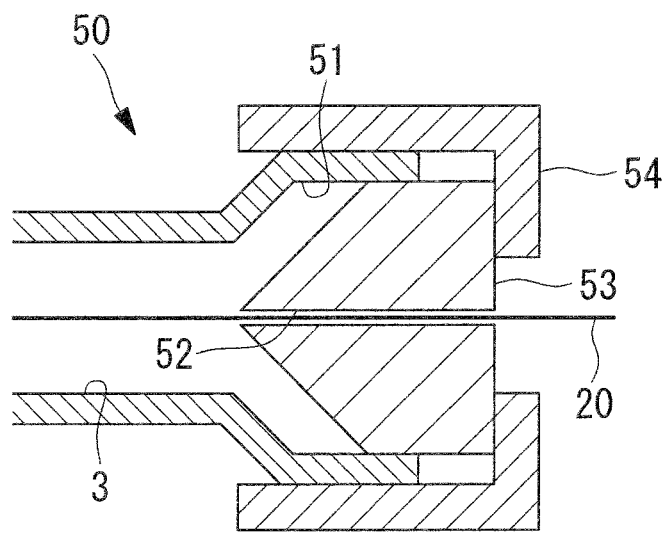
FIG. 2A and FIG. 2B are diagrams showing an example of the configuration of a fixing portion in FIG. 1, showing a state in which a guide wire is released (FIG. 2A) and a state in which the guide wire is fixed (FIG. 2B), respectively.
Figure 2B:
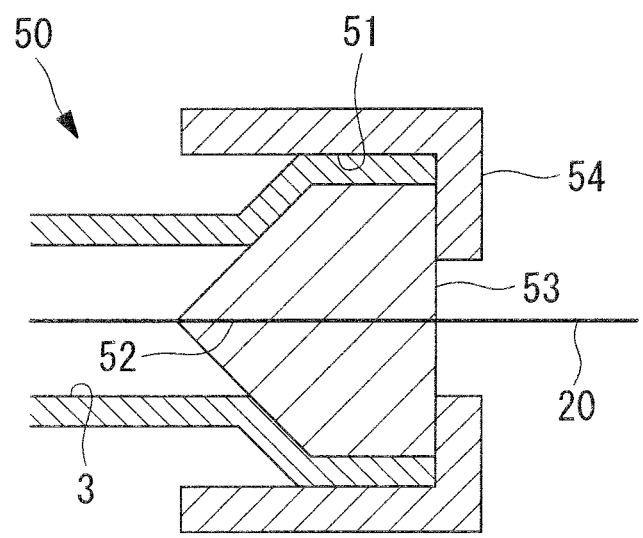

A fixing portion (movement restricting mechanism) 50 that fixes the position of the guide wire 20 is provided at the proximal end of the channel 3 of the endoscope 1. As shown in FIG. 2A, for example, the fixing portion 50 is equipped with an opening 51 communicating with the interior of the channel 3 and tapered gradually toward the interior of the channel 3, a rubber plug 53 inserted in the opening 51, through which a hole 52 is formed in substantially the center, and a cap 54 fixed to the rubber plug 53. The cap 54 is attached to the opening 51 with a screw mechanism (not shown). When the operator rotates the cap 54 in a closing direction, with the guide wire 20 inserted in the hole 52, the rubber plug 54 is inserted into the opening 51, and thus, as shown in FIG. 2B, the guide wire 20 is tightened by the inner surface of the narrowed hole 52.

The guide unit 10 is provided with a long narrow tube (tube member) 11 that can be inserted into the pericardial cavity A. The tube 11 has a first lumen 12 and a second lumen 13 formed therethrough along the longitudinal direction. The guide wire 20 is inserted into the first lumen 12, and the surgical instrument 30 is inserted into the second lumen 13.

Figure 3A:
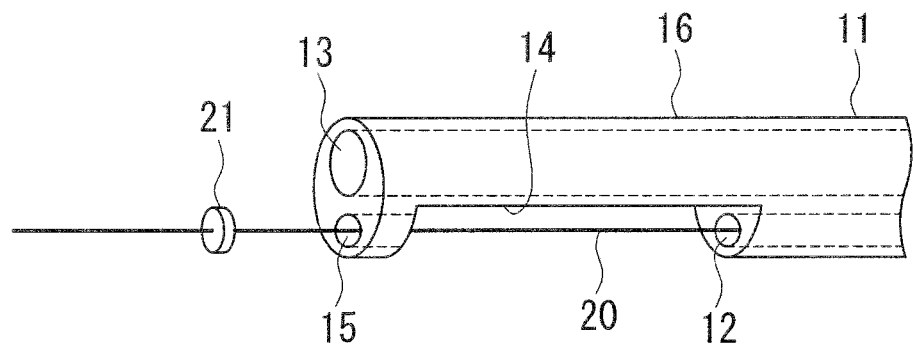
FIG. 3A and FIG. 3B are diagrams illustrating the operation of a curved portion formed at the distal end of a guide unit in FIG. 1, showing a state in which it extends in a substantially straight line (FIG. 3 A) and a state in which it curves (FIG. 3B), respectively.

As shown in FIG. 3A, the tube 11 has a groove 14, along a portion of the distal end, in the side surface. Thus, the first lumen 12 is formed at an intermediate position of the distal end, and a portion of the guide wire 20 is exposed outside the tube 11. That is, the portion at which the groove 14 is formed has a higher flexibility than the other part. Furthermore, the tube 11 has a through-hole 15, at the distal end, through which the guide wire 20 is passed.

Figure 3B:
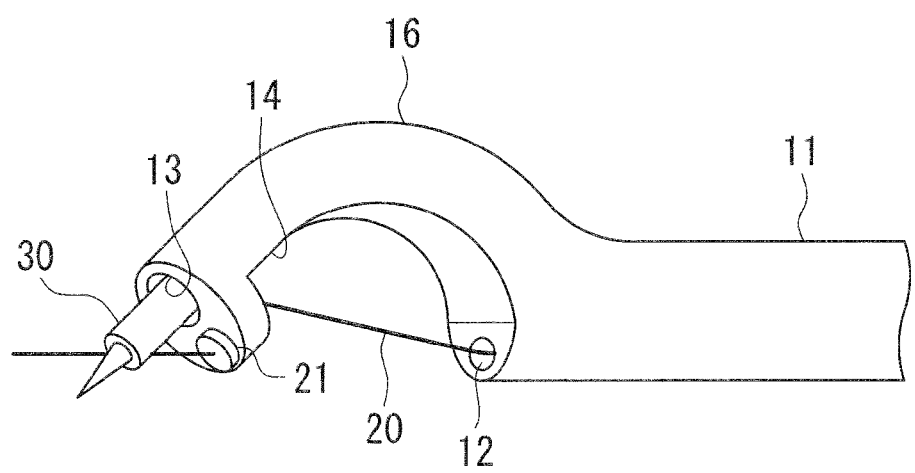

Thus, as shown in FIG. 3B, the portion where the groove 14 is formed is easily curved by pushing the tube 11, with the distal end of the tube 11 abutted against a first stopper (to be described later) 21, or by drawing the guide wire 20 to apply a longitudinal compressive force to the tube 11. In other words, the portion where the groove 14 is formed constitutes a curved portion 16. In the state in which the curved portion 16 is curved in this way, the surgical instrument 30 can be taken in and out of the first lumen 12 in a slanting direction with respect to the longitudinal direction of the tube 11. This allows even a relatively deep position from the surface of the heart B to be easily treated by the surgical instrument 30. For example, when a syringe is used as the surgical instrument 30, a medical agent can be injected into a relatively deep position from the surface of the heart B.

Figure 4:
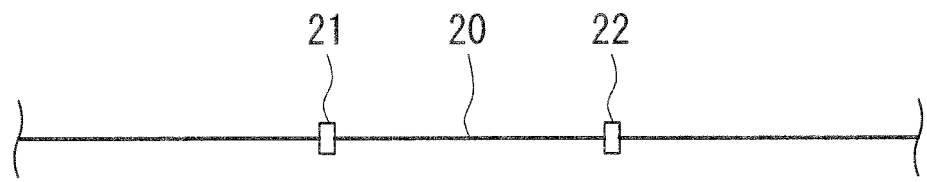
FIG. 4 is a diagram showing stoppers provided on the guide wire in FIG. 1.

As shown in FIG. 4, the guide wire 20 is equipped with the first stopper 21 and a second stopper 22 disposed at intermediate positions in the longitudinal direction, at a certain distance therebetween. The first stopper 21 has a larger outside diameter than the inside diameter of the channel 3, and the second stopper 22 has a larger outside diameter than the inside diameter of the through-hole 15 of the tube 11. The distance between the first stopper 21 and the second stopper 22 is determined depending on the depth of field of the endoscope 1 so that the endoscope 1 can focus on the surgical instrument 30 taken in and out of the second lumen 13.

Figure 5:
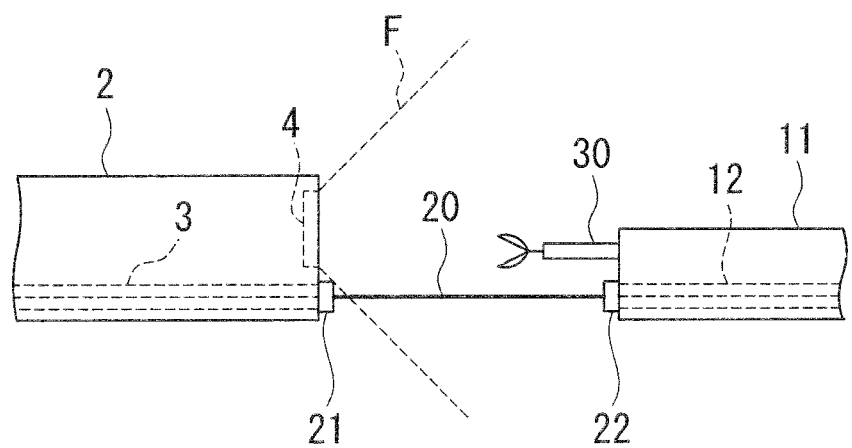
FIG. 5 is a diagram illustrating the positional relationship between an endoscope and the guide unit inserted to the positions of the stoppers in FIG. 4.

Thus, the inserted portion 2 and the tube 11 inserted from the ends of the guide wire 20 to positions at which they abut against the stoppers 21 and 22 along the guide wire 20, respectively, are disposed with an appropriate observation distance therebetween, as shown in FIG. 5. The outside diameters of the first stopper 21 and the second stopper 22 are individually designed so that the observation window 4 and an illumination window (not shown) provided at the distal end face of the inserted portion 2 and the opening of the second lumen 13 of the tube 11 are not covered by the stoppers 21 and 22, respectively, in this state.

Figure 6:
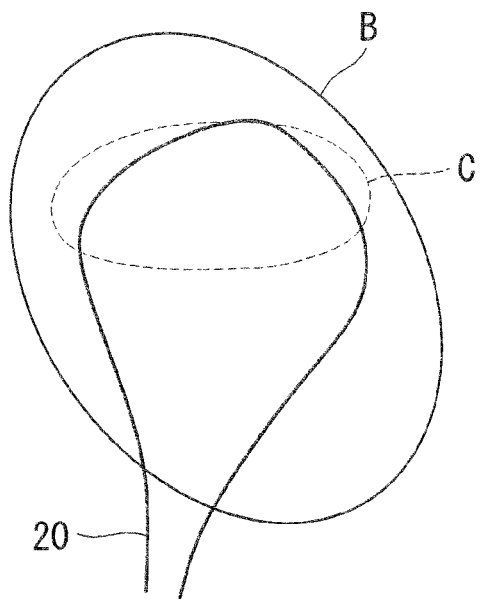
FIG. 6 is a diagram illustrating the relationship between the position of the affected part of the heart and the curved shape of the guide wire.
Figure 7:
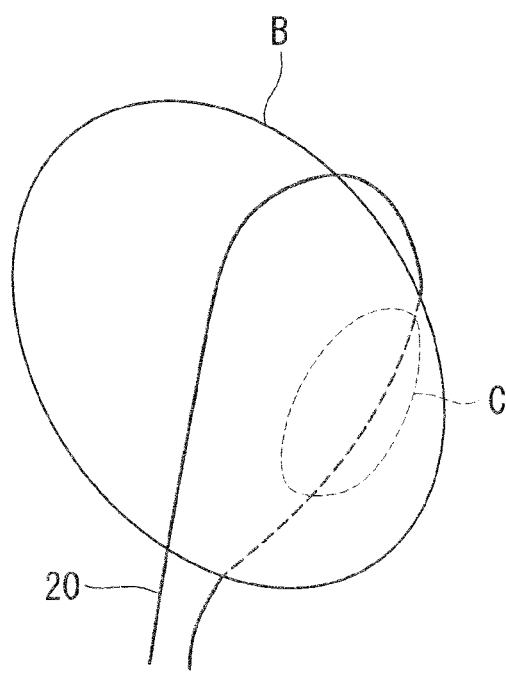
FIG. 7 is a diagram illustrating another relationship between the position of the affected part of the heart and the curved shape of the guide wire.

Furthermore, the guide wire 20 is shaped in a substantially U-shape in advance at an intermediate position in the longitudinal direction depending on the position of the affected part of the heart B. For example, in the case where an affected part C is present at the front wall of the heart B, the guide wire 20 is shaped in a substantially U-shape curve of a relatively large curvature so as to be folded back at an intermediate point on the front wall, as shown in FIG. 6. On the other hand, in the case where the affected part C is present at the back wall of the heart B, the guide wire 20 is shaped in a substantially U-shape curve of a relatively small curvature so as to make substantially one circuit of the outside of the heart B and loop back, as shown in FIG. 7.

This allows the operator to place the guide wire 20 easily along a desired path when inserting the guide wire 20 into the pericardial cavity A. Furthermore, the position of the affected part B can easily be selected just by changing the shape of the curve of the guide wire 20.

At least part at an intermediate position of the guide wire 20 may be formed of a shape-memory alloy so that the curved shape of the guide wire 20 is reproduced more accurately in the pericardial cavity A.

Furthermore, the guide wire 20 has a lower flexibility at at least the curved portion than the inserted portion 2 and the tube 11. This allows the inserted portion 2 and the tube 11 to be accurately guided along a desired route ensured by the guide wire 20 without the guide wire 20 being bent to change in shape when the inserted portion 2 and the tube 11 are inserted along the guide wire 20. Illustrations of the stoppers 21 and 22 are omitted in FIGS. 6 and 7.

Next, a medical-device guiding method using the thus-configured medical-device guiding system 100 will be described with reference to FIGS. 8 to 11.

The medical-device guiding method according to this embodiment includes a U-shape forming step S1 of placing the guide wire 20 in a substantially U-shape in the pericardial cavity A, an a endoscope inserting step S2 and guide-unit inserting step S3 of inserting the inserted portion 2 and the tube 11 into the pericardial cavity A along the guide wire 20, respectively, and an opposing step S4 of opposing the distal end of the inserted portion 2 and the distal end of the tube 11.

The U-shape forming step S1 is performed by inserting the guide wire 20 and a gripper 60 from the surface of the body D of the patient into the pericardial cavity A through two sheaths 40 inserted into the pericardial cavity A and manipulating the guide wire 20 and the gripper 60 while they are viewed on an X-ray radiographic image.

Specifically, first, the sheaths 40 are inserted into the body from below the xiphoid process and are passed through at different positions, in the vicinity of the apex of the heart, of the pericardium E into the pericardial cavity A (sheath inserting step).

Figure 8:
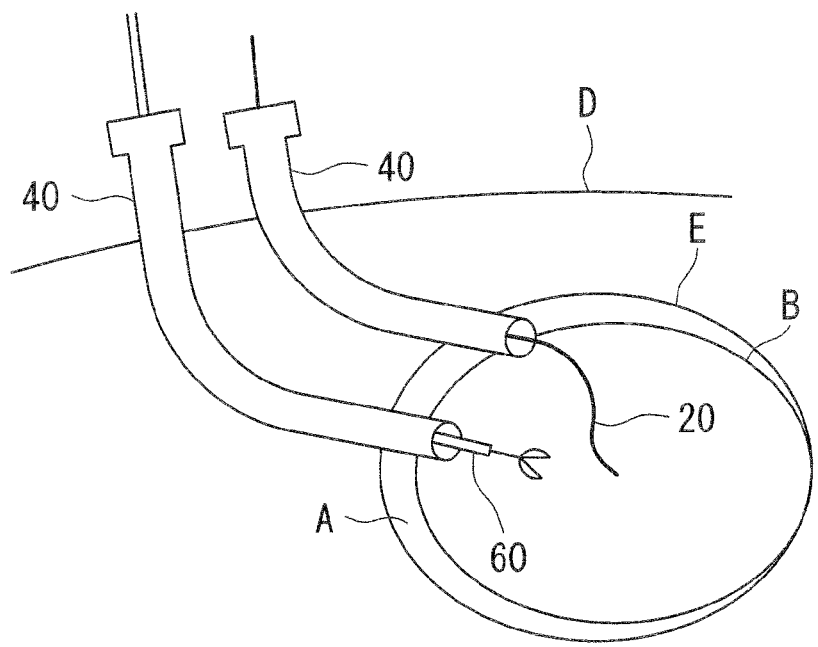
FIG. 8 is a diagram illustrating a sheath inserting step and a guide-wire inserting step of a medical-device guiding method using the medical-device guiding system in FIG. 1.
Figure 9:
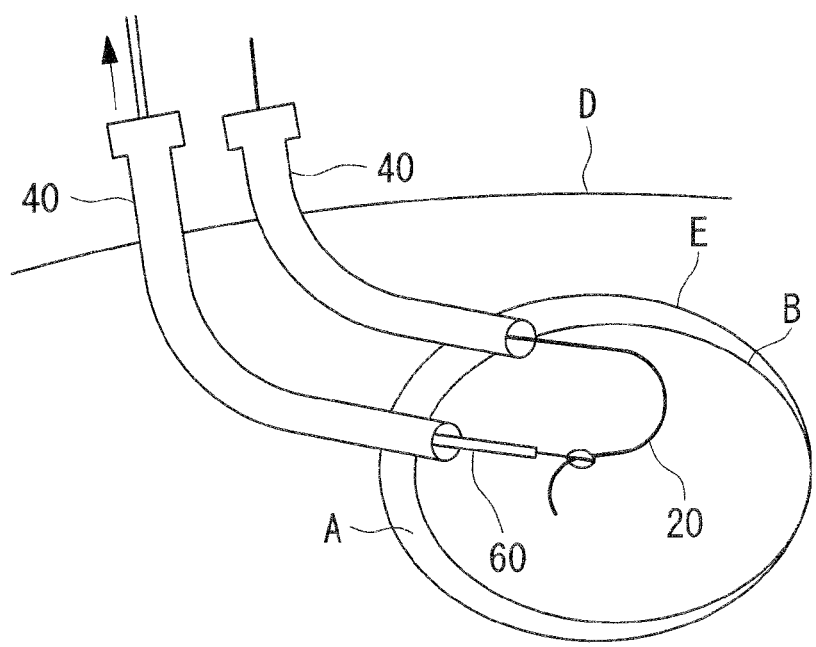
FIG. 9 is a diagram illustrating a grasping step of the medical-device guiding method using the medical-device guiding system in FIG. 1.

Next, as shown in FIG. 8, the guide wire 20 and the gripper 60 are inserted into the pericardial cavity A through one sheath 40 and the other sheath 40, respectively (guide-wire inserting step). The gripper 60 should be a device that can easily grip the guide wire 20; for example, forceps, a snare, and a basket are preferably used. Next, as shown in FIG. 9, the distal end of the guide wire 20 is gripped with the gripper 60 (grasping step). Next, the gripper 60 is drawn out of the body, with the guide wire 20 gripped, through the other sheath 40 (extracting step).

Figure 10:
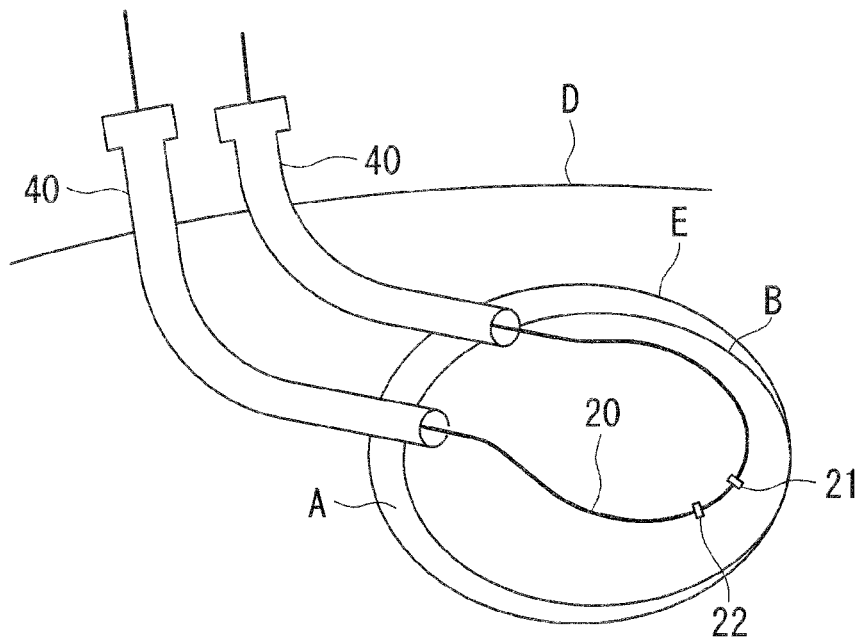
FIG. 10 is a diagram illustrating an extracting step of the medical-device guiding method using the medical-device guiding system in FIG. 1.
Figure 11:
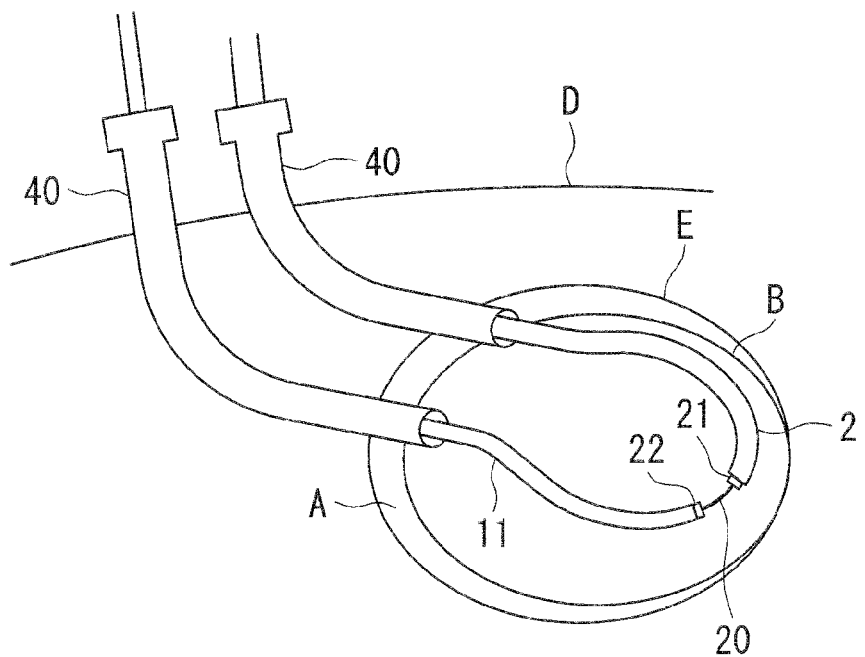
FIG. 11 is a diagram illustrating an opposing step of the medical-device guiding method using the medical-device guiding system in FIG. 1.

Through the above procedure, as shown in FIG. 10, both ends of the guide wire 20 are placed outside the body, and the intermediate position is shaped in advance and disposed in a substantially U-shape in the pericardial cavity A. Next, the inserted portion 2 and the tube 11 are inserted into the pericardial cavity A from the individual ends of the guide wire 20 through the individual sheaths 40, and the inserted portion 2 and the tube 11 are located at positions where they abut against the first and second stoppers 21 and 22, respectively (opposing step). Thus, as shown in FIG. 11, the observation window 4 provided on the distal end face of the inserted portion 2 and the distal end of the tube 11 substantially face each other, with an appropriate observation distance therebetween.

Figure 12A:
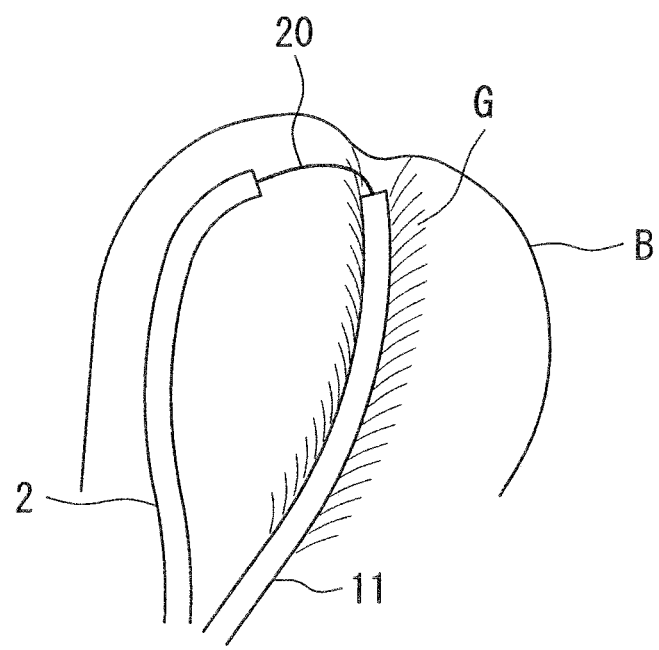
FIG. 12A is a diagram illustrating a state in which one of an inserted portion and a tube is fitted into a groove in the surface of the heart.
Figure 12B:
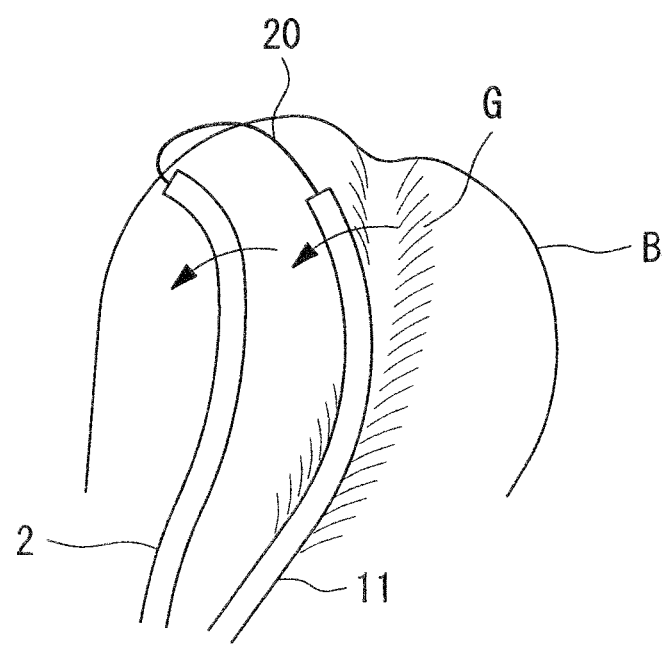
FIG. 12B is a diagram illustrating a method for extracting one from the groove by manipulating the other.

If one of the inserted portion 2 and the tube 11 is fitted into the groove G in the process of running the inserted portion 2 or the tube 11 along the guide wire 20, as shown in FIG. 12A, the other is manipulated laterally with respect to the inserting direction. Thus, one is drawn laterally with the guide wire 20 to allow the other to be easily taken out of the groove G, as shown in FIG. 12B.

The operator inserts the surgical instrument 30 into the pericardial cavity A through the second lumen 13 of the tube 11 while observing an endoscopic image displayed on a monitor. At that time, the operator observes the surgical instrument 30 taken in and out of the second lumen 13 from the front. That is, the distal end of the surgical instrument 30 and the affected part B are not hidden in the endoscopic image by the mantle of the surgical instrument 30. This therefore allows the operator to accurately treat the affected part B while easily observing the state of treatment of the affected part B in the endoscopic image with the surgical instrument 30.

In this case, the inserted portion 2 and the surgical instrument 30 can be independently manipulated in the front-to-back direction and in the circumferential direction. This therefore allows the operator, for example, to adjust the orientation or the position in the front-to-back direction of the surgical instrument 30, with the field of view of the endoscopic image fixed to the affected part B, or to change the field of view by moving the inserted portion 2, with the position of the surgical instrument 30 maintained. Thus, this has an advantage in that the inserted portion 2 and the surgical instrument 30 can easily be manipulated individually to desired positions and orientations. Furthermore, the use of separate sheaths 40 for the inserted portion 2 and the tube 11 allows narrow sheaths to be used as the sheaths 40. That is, this reduces the sizes of perforations formed in the pericardium E, and thus, those perforations are easily closed after the surgical operation, thus reducing the load on the patient.

The method for placing the guide wire 20 in a substantially U-shape in the pericardial cavity A, described in this embodiment, is merely an example, and another method may be employed.

Figure 13:
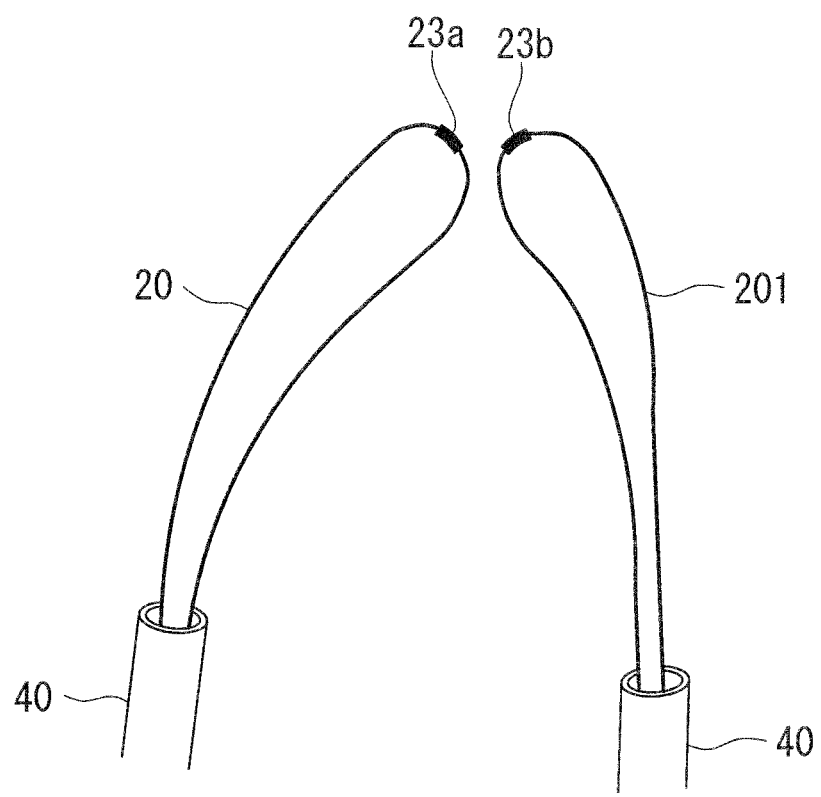
FIG. 13 is a diagram illustrating a method for placing a guide wire having magnets at intermediate positions in a substantially U-shape in the pericardial cavity.

FIG. 13 is a diagram illustrating a method of using another guide wire 201 instead of the gripper 60. The guide wires 20 and 201 have magnets 23a and 23b that generate magnetic attractive forces to each other at intermediate positions. The guide wires 20 and 201 are folded back at intermediate positions and inserted into the sheaths 40, with the folded portions at the heads. The guide wire 20 is grasped by the other guide wire 201 in the pericardial cavity A using the magnetic attractive forces of the magnets 23a and 23b. By extracting the other guide wire 201 out of the body through the sheath 40, the guide wire 20 is placed in a substantially U-shape in the pericardial cavity A.

This allows the guide wire 20 to be relatively easily detected and grasped in the pericardial cavity A. Furthermore, although it is difficult to manipulate the guide wire 20 laterally in the pericardial cavity A, the individual guide wires 20 and 201 can also easily be manipulated laterally by pushing and drawing the ends of the loop-shaped guide wires 20 and 201.

Figure 14:
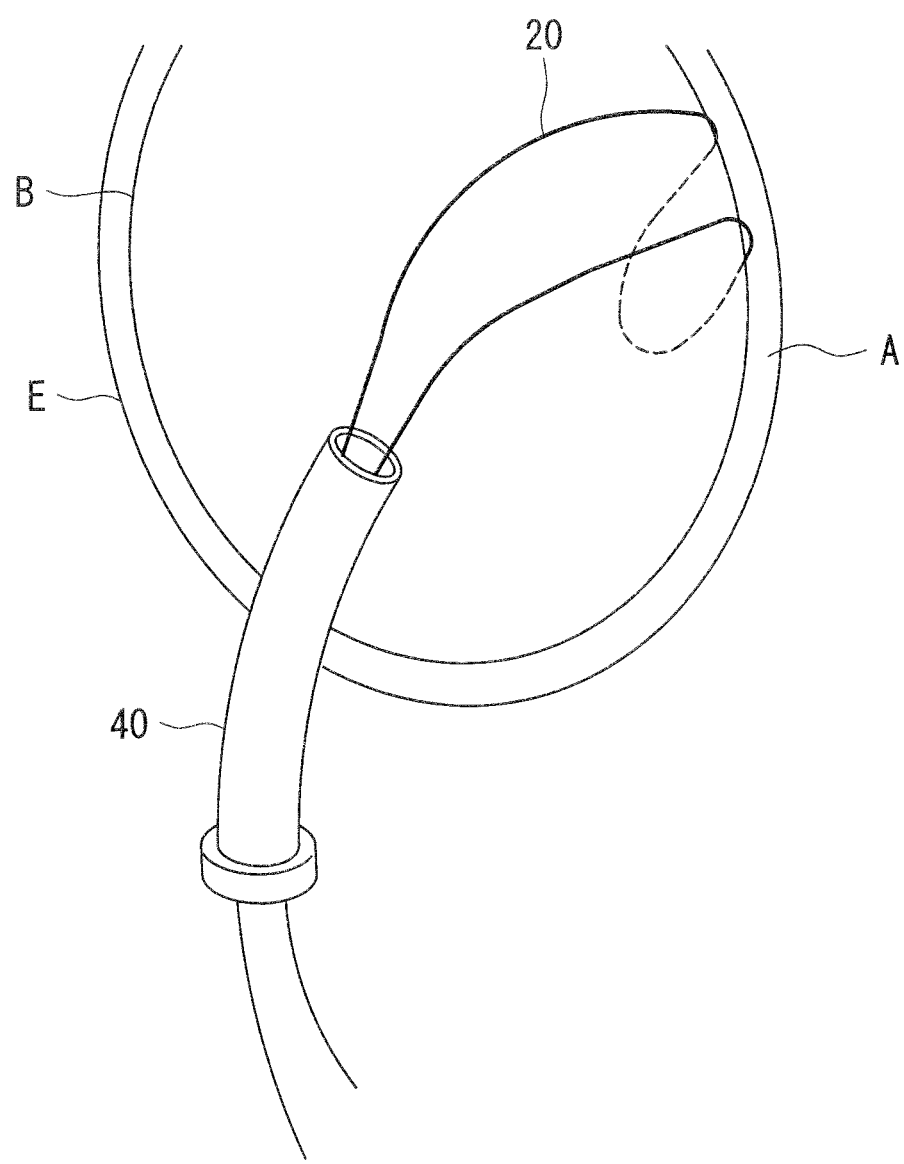
FIG. 14 is a diagram illustrating a method for placing a guide wire in a substantially U-shape in the pericardial cavity using one sheath.

FIG. 14 is a diagram illustrating a method for using one sheath 40. This method uses a sheath 40 having an inside diameter that allows both the inserted portion 2 and the tube 11 to be inserted at the same time. In this case, by folding back the guide wire 20 at an intermediate position and inserting it into the sheath 40, with the folded position at the head, the need to search for the guide wire 20 and grasping it in the pericardial cavity A is eliminated, thus allowing the guide wire 20 to be placed in a substantially U-shape by a simple manipulation.

Another example is to use another endoscope having a channel for a gripper, instead of the gripper 60. For example, after the other endoscope is inserted into the pericardial cavity A, and the guide wire is found using an endoscopic image, the gripper is inserted into the pericardial cavity A through the channel and the guide wire is grasped, and the gripper and one end of the guide wire are drawn out of the body through the channel. By performing the manipulation while observing it using the endoscopic image in this way, the manipulation can be performed more easily and more reliably as compared with the case of manipulating the guide wire 20 and the gripper 60 while confirming the position thereof on an X-ray radiographic image.

Furthermore, a sheath 40 whose distal end curves may be used so that the guide wire 20 can be taken in and out in a desired direction in the pericardial cavity A. In this case, by placing two sheaths whose distal ends curve so that the distal end faces are opposed to each other in the pericardial cavity, the guide wire that is taken in and out of one sheath can easily be introduced into the other sheath and can be taken out of the body.

Figure 15:
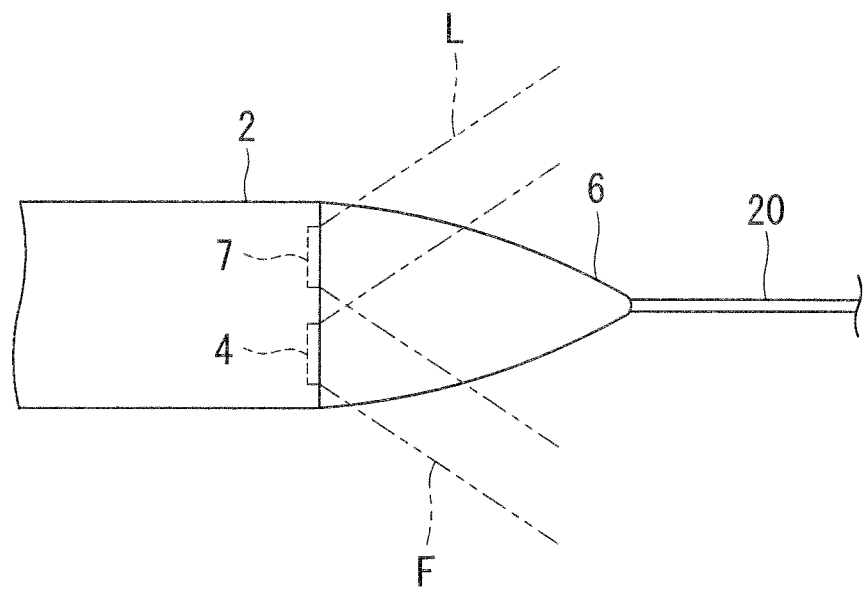
FIG. 15 is a diagram showing the configuration of a modification of an endoscope, in which a guide wire is provided at the distal end.
Figure 16:
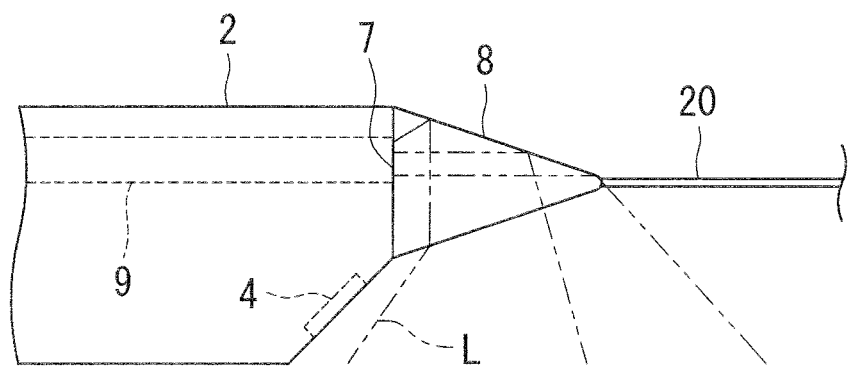
FIG. 16 is a diagram showing the configuration of another modification of an endoscope, in which the guide wire is provided at the distal end.

Furthermore, this embodiment may use the endoscope 1 in which the guide wire 20 is fixed to the distal end of the inserted portion 2, as shown in FIG. 15 or 16. Thus, when the guide wire 20 is inserted into the sheath 40 and the pericardial cavity A, the inserted portion 2 can also be inserted following the guide wire 20. That is, this eliminates the need for the channel 3 for the guide wire 20, thus allowing the diameter of the inserted portion 2 to be decreased. Furthermore, after the guide wire 20 is placed in a substantially U-shape in the pericardial cavity A and one end thereof is taken out of the body, the inserted portion 2 can easily be manipulated by pushing and drawing the one end.

In this case, the distal end of the inserted portion 2 is formed in a conical shape whose diameter decreases gradually toward the distal end so that the inserted portion 2 easily passes through a small perforation of the pericardium E through which the guide wire 20 passes. For example, as shown in FIG. 15, a conical cap 6 formed of an optically transparent material, such as glass, may be provided at the distal end thereof.

Alternatively, as shown in FIG. 16, the distal end face may have an inclination, and a conical optical member 8 may be provided at the front of an illumination window 7. Reference sign 9 denotes an optical fiber that guides illuminating light L from a light source (not shown) disposed outside the body. In this case, to efficiently illuminate a region at the observation window 4 side, it is preferable that the surface of the optical member 8 opposite to the observation window 4 be a mirror that reflects the illuminating light L. The optical member 8 may contain a light diffusing agent, such as silica particles, so as to uniformly diffuse the illuminating light L reflected by the mirror.

The configuration of the distal end of the inserted portion 2, as shown in FIG. 15 or 16, can ensure the optical path between the field of view F and the observation window 4 and the illumination window 7 without increasing the diameter of the distal end.

The guide wire 20 shown in FIGS. 15 and 16 may be detachably provided at the distal end of the inserted portion 2. This allows the guide wire 20 to be easily replaced with one having different specifications, such as rigidity, length, and outside diameter, thus allowing the guide wire 20 suitable for the surgical procedure to be used.

Figure 17A:
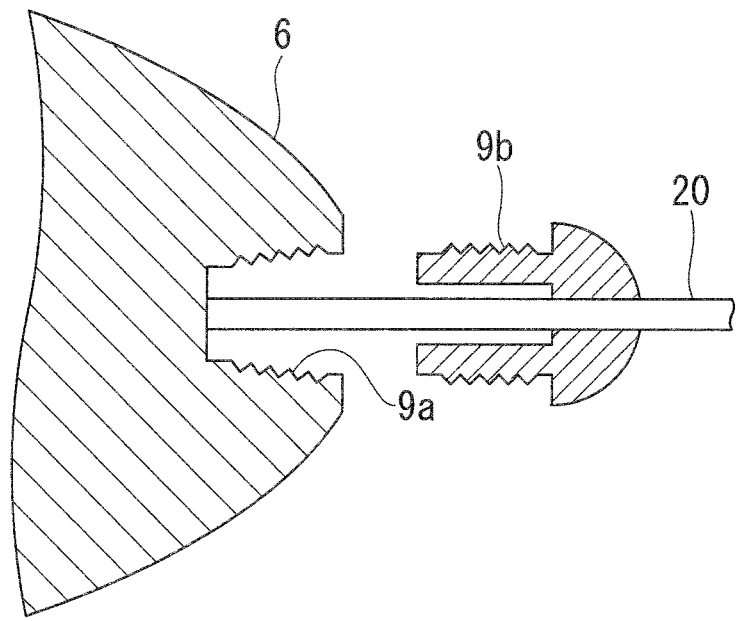
FIG. 17 is a diagram showing an example of a configuration in which a guide wire is detachably provided at the distal end of the inserted portion of the endoscope in FIG. 15.
Figure 17B:
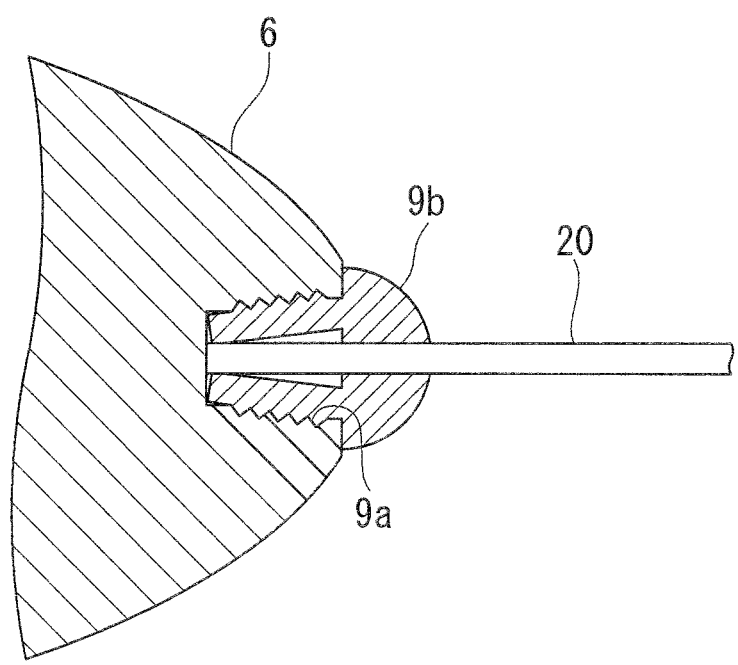

An example of a configuration for detachably attaching the guide wire 20 to the distal end of the inserted portion 2 is shown in FIGS. 17A and 17B, for example, in which an internal thread 9a is provided at the end of the cap 6, and the guide wire 20 is movably inserted into a through-hole formed along the central axis of an external thread 9b. The internal thread 9a decreases in diameter toward the proximal end. The external thread 9b is formed of a flexible material and has a longitudinal cut in part in the circumferential direction so that the opposing sides are parallel to each other in the normal state (see FIG. 17A); however, the opposing sides come close to each other when the external thread 9b engages with the internal thread 9a (see FIG. 17B). By bringing the external thread 9b into engagement with the internal thread 9a, with the guide wire 20 inserted into the through-hole, the guide wire 20 is secured by the inner surface of the external thread 9b and is fixed to the cap 6.

Furthermore, the guide wire 20 may be fixed to the distal end of the tube 11, instead of the inserted portion 2. In this case, the tube 11 is inserted into the pericardial cavity A following the guide wire 20, which therefore eliminates the need for the first lumen 12, thus decreasing the diameter of the tube 11.

Figure 18A:
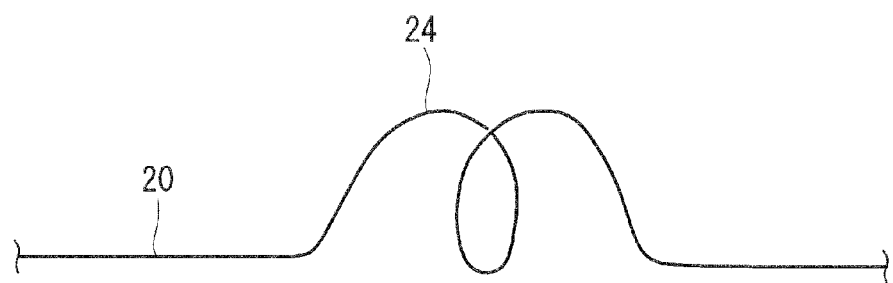
FIG. 18A is a diagram showing a modification of a guide wire, in which a loop-shaped protruding portion is provided.

Furthermore, this embodiment shows the guide wire 20 having the two stoppers 21 and 22 by way of example; alternatively, the guide wire 20 may have a protruding portion that curves in a convex shape with a predetermined curvature at an intermediate position. A protruding portion 24 may be shaped like a loop, as shown in FIG. 18A, or may be substantially semicircular, as show in FIG. 19A.

Figure 18B:
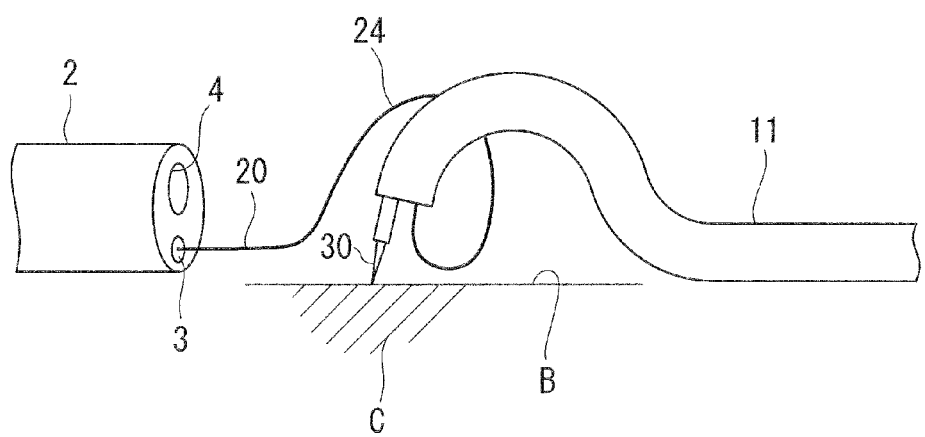
FIG. 18B is a diagram illustrating a method for using the guide wire in FIG. 18A.
Figure 19A:
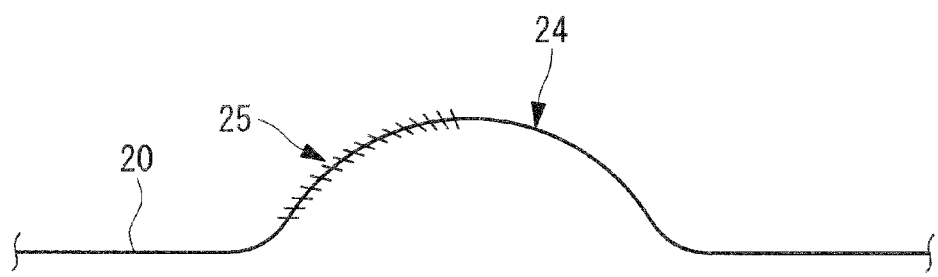
FIG. 19A is a diagram showing a modification of a guide wire, in which a semicircular protruding portion is provided.
Figure 19B:
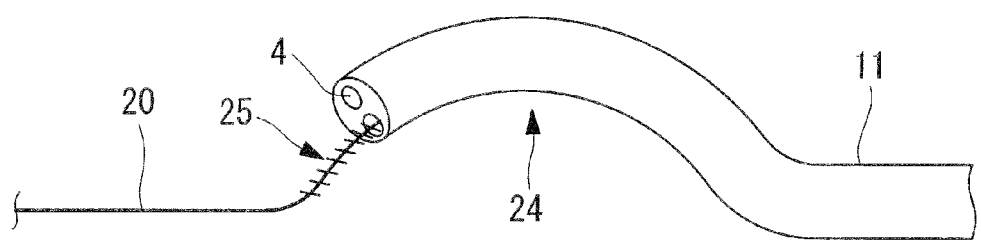
FIG. 19B is a diagram illustrating a method for using the guide wire in FIG. 19A.

This allows the distal end of the tube 11 to be placed at a certain distance from the surface of the heart B at a certain angle to the surface of the heart B at the protruding portion 24, as shown in FIGS. 18B and 19B. That is, even with the tube 11 that does not have the curved portion 16, a relatively deep position from the surface of the heart B can be treated.

In the configuration having the protruding portion 24, the protruding portion 24 may have an external threaded portion (movement restricting mechanism) 25, and the second lumen 13 has therein an internal threaded portion (not shown, movement restricting mechanism) that comes into engagement with the external threaded portion 25, as shown in FIG. 19A. This allows the position and the angle relative to the surface of the heart B to be easily and accurately adjusted by rotating the tube 11 in the circumferential direction. Furthermore, this allows the position of the tube 11 to be held stably irrespective of pulsation.

Figure 20:
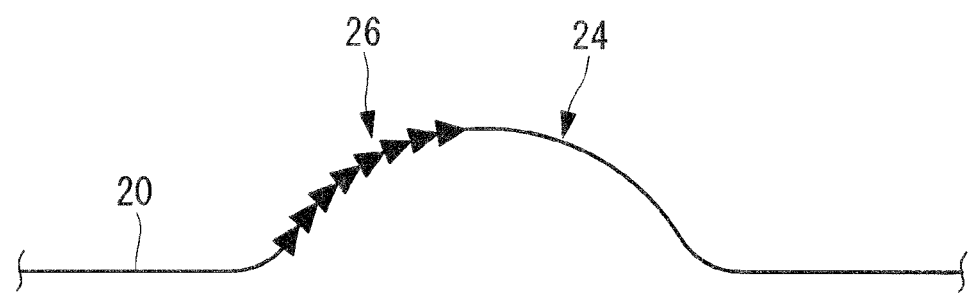
FIG. 20 is a diagram showing another modification of a guide wire having a semicircular protruding portion.

Furthermore, instead of the external threaded portion 25 and the internal threaded portion, a ratchet mechanism, that is, a row of teeth (movement restricting mechanism) 26 arranged in the longitudinal direction of the protruding portion 24, and a protruding portion (not shown, movement restricting mechanism) which is provided in the second lumen 13 and coming into engagement with recessed portions formed between adjoining teeth of the row of teeth 26, as shown in FIG. 20. In the case where the ratchet mechanism is provided, it is preferable to provide a release mechanism for releasing the restriction on backward movement.

Figure 21:
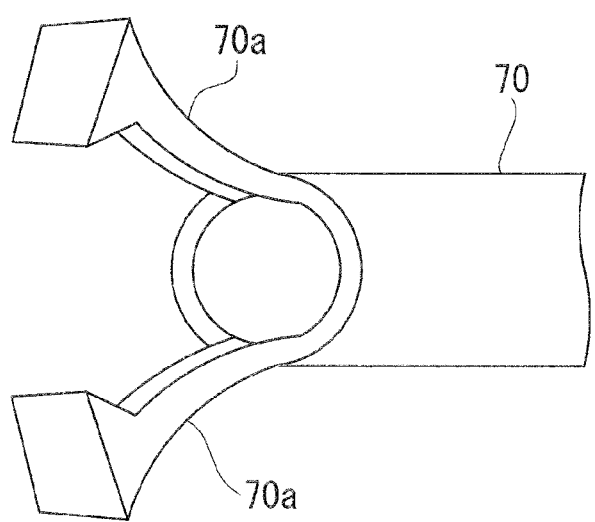
FIG. 21 is a diagram showing an example of the configuration of a release mechanism.
Figure 22A:
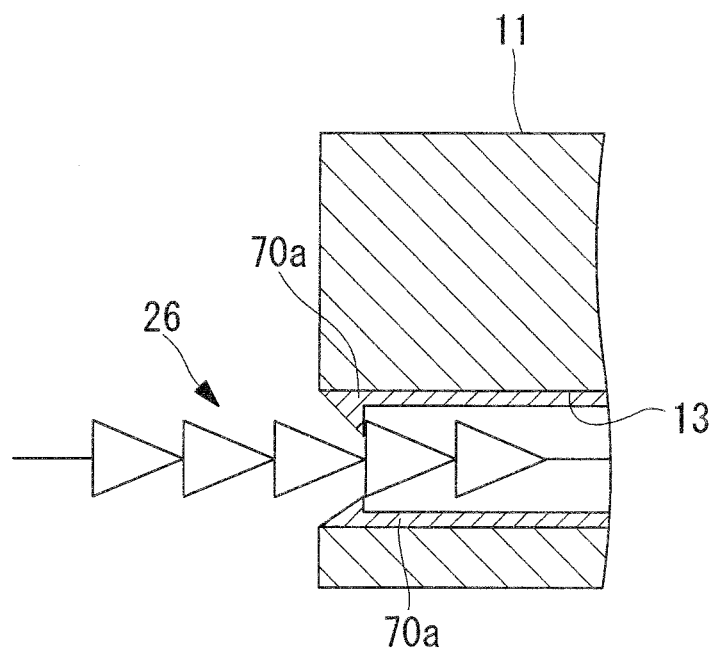
Figure 22B:
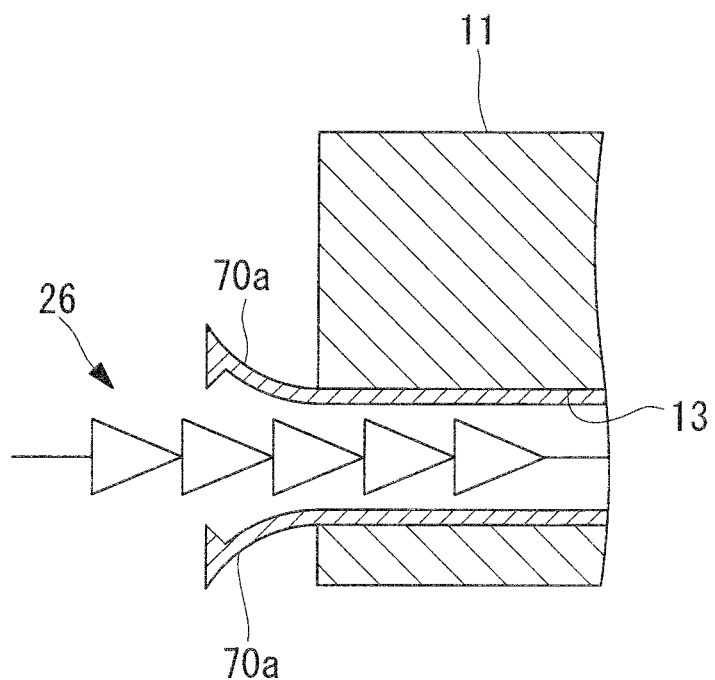

An example of the release mechanism is a catheter 70, which is accommodated in the second lumen 13 and whose distal end can be expandable outward in the radial direction due to its elasticity, as shown in FIG. 21. An example of the distal end of the catheter 70 is a plurality of (two in the illustrated example) portions 70a arranged in the circumferential direction and shaped in an outward warped form. The ends of the portions 70a are shaped like hooks to form protruding portions. Thus, the distal ends of the catheter 70 become a substantially straight line in the second lumen 13, and thus, the ends of the portions 70a come into engagement with the recessed portions of the row of teeth 26, as shown in FIG. 22A. When the distal ends of the catheter 70 are taken in and out of the second lumen 13, they expand in the radial direction to positions away from the row of teeth 26, as shown in FIG. 22B, thus allowing the guide wire 20 to assume a retractable state.

Figure 23:
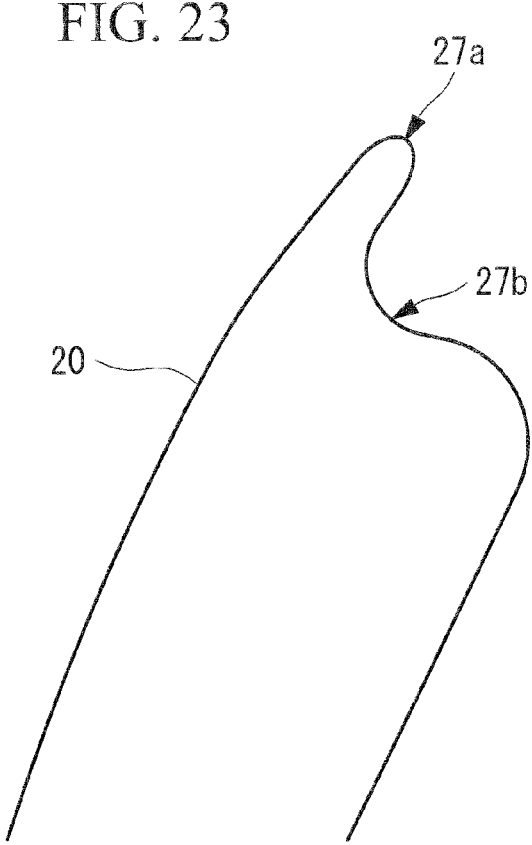
FIG. 23 is a diagram showing a modification of a guide wire, in which a first curved portion and a second curved portion are provided.
Figure 24:
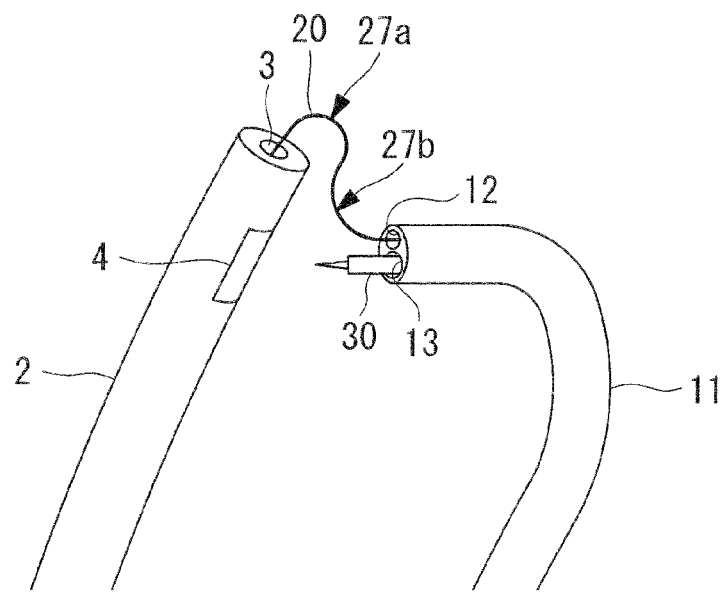
FIG. 24 is a diagram illustrating a method for using the guide wire in FIG. 23.

Furthermore, as shown in FIG. 23, the guide wire 20 may have, at an intermediate position, a first curved portion 27a that curves in a substantially U-shape and a second curved portion 27b at which one end of the first curved portion 27a curves at a predetermined angle with respect to the other end, at substantially 90° in the illustrated example. With such a guide wire 20, by inserting the inserted portion 2 and the tube 11 to positions at which they abut at the first curved portion 27a and the second curved portion 27b, respectively, the inserted portion 2 and the surgical instrument 30 can be disposed at a predetermined angle. That is, such a guide wire 20 is suitably used in the case where a side-view type having the observation window 4 on the side of the distal end is used as the endoscope 1, as shown in FIG. 24, and in the case where an ablation catheter or the like having an electrode 31 on the side is used as the surgical instrument 30, as shown in FIG. 25.

Figure 25:
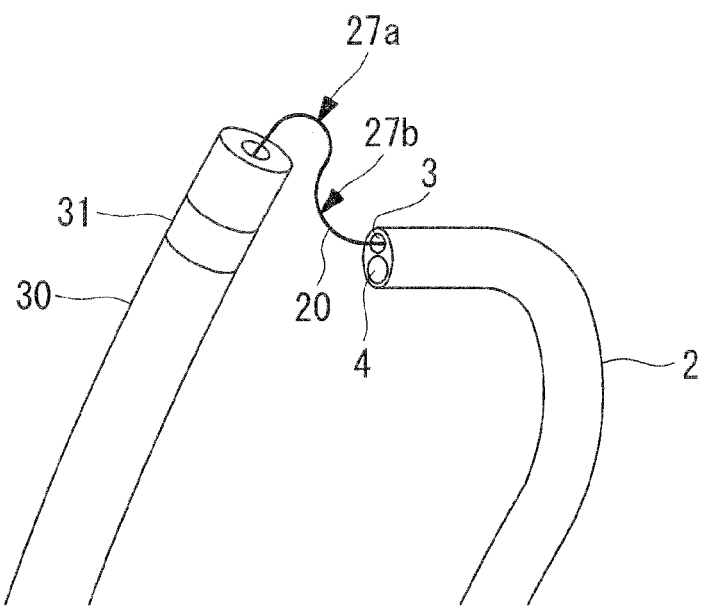
FIG. 25 is a diagram illustrating another method for using the guide wire in FIG. 23.
Figure 26:
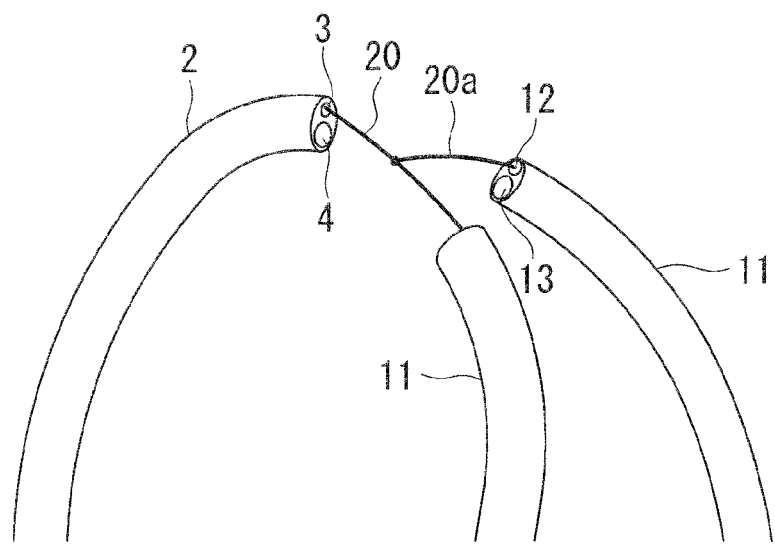
FIG. 26 is a diagram illustrating a method for using a guide wire having a branch wire.

Although this embodiment shows the case where one endoscope 1 and one guide unit 10 are used by way of example, the endoscope 1 and the guide unit 10 using a guide wire 20 having at least one branch wire 20a at an intermediate position, three or more in total, may be used, as shown in FIG. 25. An example of the branch wire 20a is a wire connected to an intermediate position of one guide wire 20. Thus, even in the case where two surgical instruments are used at the same time during observation with the endoscope 1, for example, the states of treatment using the individual surgical instruments can easily be observed from substantially the front.

What is claimed is:

1. A medical-device guiding system comprising:
   a guide wire having the flexibility of being able to curve in a substantially U-shape in a pericardial cavity;
   an endoscope having a long narrow inserted portion which can be inserted into the pericardial cavity and in which a channel in which the guide wire is inserted is formed in the longitudinal direction; and
   a guide unit including a long narrow tube member which can be inserted into the pericardial cavity and in which a first lumen in which the guide wire is inserted and a second lumen in which a surgical instrument is inserted are formed in the longitudinal direction,
   wherein the medical-device guiding system further comprises a sheath into which the endoscope or the guide unit is individually inserted,
   wherein the inserted portion includes an observation window provided at the distal end face thereof,
   wherein the guide wire has two stoppers provided at intermediate positions in the longitudinal direction, with a distance corresponding to a depth of field of the endoscope therebetween, and having outside diameters larger than diameters of openings at the distal ends of the channel and the first lumen,
   wherein the two stoppers are provided without covering the observation window and an opening at the distal end of the second lumen,
   wherein the two stoppers are inserted into the pericardial cavity through the sheath and are disposed with said distance therebetween, and
   wherein the inserted portion and the tube member are inserted into the pericardial cavity and are located at positions where they abut against individual stoppers, respectively, and the distal end of the inserted portion and the distal end of the tube member substantially face each other, with said distance therebetween.

2. The medical-device guiding system according to claim 1, wherein the surgical instrument that is taken out of the second lumen within said distance performs a treatment.

3. A medical-device guiding system comprising:
   an endoscope comprising:
      an inserted portion configured to be inserted into a pericardial cavity, the inserted portion of the endoscope defining a lumen along a longitudinal direction of the inserted portion of the endoscope;
      an observation window provided at a distal end face of the inserted portion of the endoscope; and
      at least one lens provided in the inserted portion of the endoscope for focusing light incident on the observation window, wherein the at least one lens has a predetermined depth of field;
   a guide unit comprising an inserted portion configured to be inserted into the pericardial cavity, the inserted portion of the guide unit defining a first lumen along a longitudinal direction of the inserted portion of the guide unit, and a second lumen along the longitudinal direction of the inserted portion of the guide unit through which a surgical instrument can be protruded from the distal end face of the inserted portion of the guide unit; and a guide wire comprising:
- a wire having a first end and a second end, wherein the wire has a flexibility to curve in the pericardial cavity;
- a first stopper arranged at a first position along the wire between the first end and the second end; and
- a second stopper arranged at a second position along the wire between the first end and the second end;
- wherein the wire is configured to be inserted from the first end of the wire into the lumen of the inserted portion of the endoscope to guide the endoscope along the wire to abut against the first stopper,
- wherein the wire is configured to be inserted from the second end of the wire into the first lumen of the inserted portion of the guide unit to guide the guide unit along the wire to abut against the second stopper,
- wherein the first position and second position along the wire are separated by a predetermined distance corresponding to the predetermined depth of field of the at least one lens of the endoscope such that in the configuration in which the endoscope is abutted against the first stopper and the guide unit is abutted against the second stopper, the at least one lens is capable of focusing on the surgical instrument protruding from the distal end face of the inserted portion of the guide unit.

* * * * *